(12) United States Patent
Steidler et al.

(10) Patent No.: US 6,190,662 B1
(45) Date of Patent: Feb. 20, 2001

(54) MATERIALS AND METHODS RELATING TO THE ATTACHMENT AND DISPLAY OF SUBSTANCES ON CELL SURFACES

(75) Inventors: Lothar Steidler; Erik Remaut, both of Ghent (BE); Jeremy Mark Wells, Cambridge (GB)

(73) Assignee: Vlaams Interuniversitair Instituut voor Biotechnologie (VIB) vzw, Zwijnaarde (BE)

( * ) Notice: Under 35 U.S.C. 154(b), the term of this patent shall be extended for 0 days.

(21) Appl. No.: 09/036,609

(22) Filed: Mar. 6, 1998

Related U.S. Application Data (63) Continuation of application No. PCT/GB96/02195, filed on Sep. 6, 1996.

(30) Foreign Application Priority Data

Sep. 7, 1995 (GB) .................................................. 9518323

(51) Int. Cl.⁷ ........................ A61K 39/00; A61K 39/385; A61K 39/02; C12N 15/09; C12N 15/00
(52) U.S. Cl. .................................. 424/184.1; 424/192.1; 424/195.11; 424/197.11; 424/200.1; 435/69.3; 435/252.3; 435/320.1
(58) Field of Search ............................ 424/184.1, 192.1, 424/195.11, 197.11, 200.1; 435/69.3, 320.1, 252.3

(56) References Cited

U.S. PATENT DOCUMENTS 5,348,867 * 9/1994 Georgiou et al. .
5,616,686   4/1997 Fischetti et al. .

FOREIGN PATENT DOCUMENTS

WO 93/18163   9/1993 (WO) .

OTHER PUBLICATIONS

A. Charbit et al., J. Bacteriology, 173 (1): 262–275 (1991).
A. Charbit et al., J. Immunology, 139: 1658–1664 (1987).
D. Chiswell et al., TIBTECH, 10: 80–84 (1992).
G. Georgiou et al., TIBTECH, 11: 6–10 (1993).
T. Klauser et al., EMBJ Journal, 9: 1991–1999 (1990).
M.G. Kornacker et al., Mol Micro, 7: 1101–1109 (1990).
J. Marmur, J.Mol.Biol., 3: 208–218 (1961).
WW Navarre et al., Mol. Micro, 14: 115–121 (1994).
RK Saiki et al., Science, 230: 1350–1354 (1985).
O Schneewind et al., EMBO J, 12(12): 4803–4811 (1993).
D. Simon et al., Biochimie, 70: 559–566 (1988).
L. Steidler et al., Mol.Gen.Genet, 236: 187–192(1993).
L. Steidler et al., J. Bacteriology, 175(23): 7639–7643 (1993).
L. Steidler et al., Appl. Environ. Microbiol, 55: 984–993 (1989).
G. Thiry et al., Appl. Environ. Microbiol, 55(4): 984–993 (1989).
NR Waterfield et al., Gene, 165: 9–15 (1995).
JM Wells et al., Mol. Microbiol. 8(6): 1155–1162 (1993).
JM Wells et al., Environ. Microbiol. 59(11): 3954–3959 (1993).
JM Wells et al., J. Appl. Bact. 74: 629–6365 (1993).
Ngugen et al., "Cell–Surface Display of Heterologous Epitopes on *Staphylococcus Xylosus* As A Potential Delivery System For Oral Vaccination"; Gene, vol. 128, 1993, Amsterdam, NL. pp. 89–94. See page 91, fig. 1.
Samuelson, P., et al.; "Cell Surface Display Of Recombinant Proteins On *Staphylococcus Carnosus*"; Journal of Bacteriology, vol. 177, No. 6, Mar. 1995, pp. 1470–1476. See abstract; Figures 1,3.
Oggioni, M.R. et al.; "Immunization of Mice By Oral Colonization with Live Recombinant Commensal Streptococci"; Vaccine, 13 (8) pp. 775–779, Jun. 1995, England.
Steidler, L. et al.; Secretion of Biologically Active Murine Interleukin–2 by *Lactococcus Lactis* Subsp. Lactis; Appl. Environ Microbiol, Apr. 1995 (4) p1627–9, United States.

* cited by examiner

*Primary Examiner*—Albert Navarro
(74) *Attorney, Agent, or Firm*—Pennie & Edmonds LLP (57) ABSTRACT

Methods for obtaining surface expression of a desired protein or polypeptide in Gram-positive host organisms are provided. In addition, vectors useful in such methods as well as Gram-positive host organisms transformed with such vectors are disclosed.

24 Claims, 7 Drawing Sheets

FEATURES OF THE pTREX1 EXPRESSION CASSETTE

```
          Taq I                                                                        Mse I                                  Mnl I        Tfi I
EcoR I    |    Mnl I                                                                   Age I                                  |            Hinf I
Apo I   Mse I  |                                                                       ||                                     |            |
|   |   |      |                                                                       ||                                     |            |
GAATTCGATTAAGTCATCTTACCTCTTTTAGTTTTTCTTATAATCTAAATGATAACATTTTTATAATTAATCTATAAACCATATCTAAATATTAGATATATTTGGTATAGGAGAAACCTTTA
CTTAAGCTAATTCAGTAGAATGGAGAAATCAAAAAGAATATTAGATTTACTATTGTAAAAATATTAATTAGATTAGATATTTGTATAGATCTATATAAACCATATCCCTCTTTTGGAAT
|   |   |                              |                                              ||                                     |            |-  97
1   1   5                              22                                              69                                    89           -  97
                                                                                       70                                                  100

Transcription start
                                                                      point
                                            Bgl II                      |                                     Bfa I                  Mse I
                                            |                           ↓                                     |                      |
                                            |                                                                                        |
CAAAATTTATTATCTACTCCTTTGTAGATATGTTATAATACAAGTATCAGATCTCGGGAGACCACAACGGTTTCCCACTAGAAATAATTTGTTTAACTTT
GTTTTAAATAATAGATGAGGAAACATCTATACAATATTATGTTCATAGTCTAGAGCCCTCTGGTGTTGCCAAAGGGTGATCTTTATTAAAACAAATTGAAA
|                                                                   ||           157                         177                    193    200
103                                                                 149          157
                                                                    149
                                                                    150
                                                                    150
                                                                    150
                                                                    150
                                                          Fnu4H I
                                                          Msp I
                                                          Hpa II
                                                        Sau3A I
                                                        Mbo I
                                                        Dpn II
                                                        Dpn I Conserved -10 and -35
              promoter elements
```

FIG. 5C(II)

List of primers used for PCR

Sense primer for PCR of *usp45*-TTFC gene fusion
5' CATGAAAAAAAGATTATCTCAGCTATTT 3'

Antisense primer for *usp45*-TTFC gene fusion including a BamHI site for in-frame fusion to the
*S. aureus* protein A anchoring domain
5' CGGGATCCTGATCATTTGTCCATCCTTCATCTG 3'

Sense primer for *S. aureus* protein A anchoring domain
5' CGGGATCCAAAAGAGGAAGACAACAACAAG 3'

Antisense primer for *S. aureus* protein A anchoring domain
5' GAAGATCTACTAGTTATAGTTCGCGACGACG 3'

FIG. 6

FIG. 7

MATERIALS AND METHODS RELATING TO THE ATTACHMENT AND DISPLAY OF SUBSTANCES ON CELL SURFACES This is a continuation of application no. PCT/GB96/02195 filed Sep. 6, 1996, the contents of which are expressly incorporated herein by reference thereto.

FIELD OF THE INVENTION

The present invention relates to materials and methods for the exportation, cell wall attachment and display of substances, in particular proteins and polypeptides, on the cell surface of Gram-positive bacteria such as *Lactococcus lactis*. Methods are disclosed providing for the surface expression of cell wall anchoring of proteins, including antigens, specific binding proteins and enzymes.

BACKGROUND TO THE INVENTION

The display of polypeptides on the surface of bacteria has been a subject of investigation for several years. This interest has arisen because recombinant DNA technology makes it possible to use bacterial cells as factories for the inexpensive production of a wide range of different proteins. Work has centred on the display of polypeptides on the surface of Gram-negative bacteria, see for example the review provided in U.S. Pat. No. 5,348,867. However, in Gram-negative bacteria it has proved difficult to find an adaptable method of displaying polypeptides on the surface of the cells so that they are securely attached to the surface at high density.

However, high density surface expression of recombinant products on the bacterial surface is a prerequisite for the use of these bacteria in certain industrial applications, and in the areas of vaccine development, the construction of peptide libraries and the production of whole bacterial cell adsorbents. There is no prior art known to the inventors which results in the consistent, stable, high density expression on the surface of bacteria, and more especially, on the cell surface of Gram-positive bacteria such as *Lactococcus lactis* and similar or related species.

Previous work on the bacterial surface presentation of polypeptides has focused mainly on the use of Gram-negative bacterial such as *E. coli* and Salmonella (Georgiou et al., 1993). In Gram-negative bacteria the peptidoglycan cell wall is bounded by two separate lipid membranes. The outer membrane is largely impermeable to molecules with a relative molecular mass greater than 500 (Mr) and as a result very few proteins are released into the growth medium. Owing to the presence of an outer membrane, surface exposed proteins of Gram-negative bacteria are either integral outer membrane proteins or protein appendages such as pili or flagella The few proteins which are secreted by Gram-negative organisms are transported across the outer membrane by specialised transport systems which may involve up to 14 different gene products (eg pullulanase secretion; Kornacker and Pugsley 1990a).

The possibility of displaying foreign proteins by making C-terminal fusions to integral membrane proteins is complicated by the fact that the C-terminal regions of many integral membrane proteins appears to be necessary for targeting and correct assembly of the protein in the outer membrane. One way around this problem has been to use the N-terminal targeting sequence of the *E. coli* major lipoprotein (Lpp) to direct fusion proteins to the outer membrane. As Lpp does not transverse the outer membrane, the membrane spanning domain of an outer membrane protein (OMP; eg *E. coli* OmpA) is also required to localise a fusion protein to the cell surface. Nevertheless, the utility of these Lpp-OmpA fusions to display functional proteins such as β-lactamase, a single chain Fv antibody and a cellulose binding protein have been demonstrated (Georgiou et al., 1990).

Other approaches for the surface display of polypeptides have involved making amino acid insertions within outer membrane loops of integral membrane proteins such as Lam B or in the pilin and flagellin proteins which do not contain transmembrane domains (Charbit et al., 1991; Thiry et al., 1989, Steidler et al, 1993 a,b). The major problem with this approach has been that large amino acid insertions/substitutions disrupt the proper folding and/or localisation of the fusion protein in such a way that when used to immobilise the bacterial cells, the fusion proteins are extracted from the outer membrane (Steidler, PhD Thesis, University of Gent, Belgium).

Although significant progress has recently been made in the development of methods from the surface display of proteins in Gram-negative bacteria, the major drawback to the use of integral membrane proteins for such purposes is that the fusion proteins are not firmly attached to the cell surface. Furthermore, the high level expression of membrane proteins is known to be detrimental to the cell, a factor which may limit the possible applications for such systems in cases where high density surface expression is required.

In contrast, Gram-positive bacteria do not possess an outer membrane and proteins which are displayed on the cell surface are thought to be linked to the cell surface via their C-terminus (Schneewind et al., 1992). Many surface proteins of Gram-positive bacteria possess certain common features which are unique to these organisms. Each molecule has at its N-terminal end a secretion leader peptide which acts as an export signal for cell secretion, a LPXTG motif, a C-terminal hydrophobic domain and charged amino acids at the very C terminus. Most work on the characterisation and function of these has been carried out in *S. aureus* using the cell wall sorting and anchoring domains of *S. aureus* protein A (Navarre and Schneewind, 1994). It has been shown that protein A is covalently coupled to the cell wall of *S. aureus* by a mechanism which is yet to be elucidated.

SUMMARY OF THE INVENTION

The present invention demonstrates that the firm attachment of foreign proteins to the surface of *L. lactis* and other Gram-positive bacteria is made possible by constructing chimeric genes encoding a fusion protein which contains nucleic acid encoding (1) an N-terminal secretion signal, (2) the protein to be surface expressed and (3) the cell wall sorting and anchoring domains of *S. aureus* protein A.

By comparison with *E. coli*, as relatively few heterologous proteins have been expressed at high level in *L. lactis*, before the present work it was impossible to predict with certainty whether the expression of any particular protein would be possible or whether such expression would be toxic to the cell. Such toxicity is likely to occur when a secreted or membrane associated protein is expressed at high level, as protein export may adversely affect the integrity of the cell membrane or the function of the general secretory pathway.

Thus, the present invention shows for the first time that proteins or polypeptides can be firmly attached to the cell wall of Gram-positive bacteria when expressed as fusions with a cell wall anchoring domain. As is shown below, it is not possible to remove the protein by boiling the cells in the presence of an ionic detergent which would normally release non-covalently bound proteins. While not wishing to be bound by any particular theory, we believe that *L. lactis* appears to possess the necessary enzyme(s) required to link (covalently) the expressed protein A fusion to the cell wall peptidoglycan. This binding could not have been readily predicted from the possession by protein A of the LPXTG motif and C-terminal hydrophobic domains common to many surface proteins of Gram-positive bacteria, since these motifs are just necessary, but not sufficient conditions for the occurrence of covalent cell wall anchoring.

Accordingly, the present invention arises from the finding that it is possible to firmly attach proteins and polypeptides of interest (including but not restricted to adhesins, antigens, enzymes and ligands) to the outer face of the peptidoglycan cell wall of Gram-positive bacteria, such as *Lactococcus lactis*, using a chimeric gene comprising nucleic acid encoding a secretion signal sequence, a desired protein or polypeptide and a cell wall attachment domain, such as that derived from *Staphylococcus aureus* protein A.

Accordingly, in a first aspect, the present invention provides a recombinant vector including nucleic acid encoding a fusion protein comprising a secretion signal sequence, a desired protein or polypeptide and a cell wall attachment domain, so that when the vector is transformed in a Gram-positive bacterial host and the fusion protein is expressed, the desired protein or polypeptide is attached and displayed on the outer surface of the cell wall of the host.

In a further aspect, the present invention provides a Gram-positive host organism transformed with a recombinant vector as described above.

In a further aspect, the present invention provides a Gram-positive host organism described above wherein the desired protein or polypeptide has been expressed, and is covalently attached to the cell wall and is displayed on the outer face of the surface of the host organism.

In a further aspect, the present invention provides a method of engineering a Gram-positive host organism to display a desired protein or polypeptide on its surface comprising transforming the host organism with recombinant nucleic acid encoding a fusion protein comprising a secretion signal sequence, a desired protein or polypeptide and a cell wall attachment domain, so that the host is capable of expressing the fusion protein, whereby the cell wall anchoring domain enables the host to attach and display the desired protein or polypeptide on the cell wall surface. This aspect also includes strains of Gram-positive host organisms as obtainable by this method.

Preferably, the Gram-positive host organism is a Lactococcus host, such as *Lactococcus lactis*, or a similar or related species having the properties of expressing the fusion protein, and attaching and stably displaying the desired protein or polypeptide on the cell surface. The unexpected finding that the protein A fusions are similarly attached to the cell wall in *L. lactis* and *S. aureus* suggests that this will also be the case with other cell wall binding domains in similar or related Gram-positive bacteria. Examples of other such Gram-positive bacteria include *Bacillus subtilis, Streptococcus gordonii, Staphylococcus xylosus,* Lactobacillus spec. and psychrophilic and psychrotropic species of the genera Bacillus spec., Clostridium spec. and Corynebacterium spec.

Preferably, the secretion signal sequence is capable of targeting the protein for secretion via the sec dependent pathway of secretion and is derived from a signal sequence of a naturally secreted protein such as usp45. However, while this secretion signal sequence is used in the examples, other secretion signal sequences may be employed, such as those derived from other secreted proteins.

Preferably, the cell wall anchoring domain comprises, at the C-terminal, anchoring domain derived from the *Staphylococcus aureus* protein A. However, other proteins may be used as the cell wall anchoring domain, provided they have the properties of being stably bound to the surface of the cell and are capable of representing the desired protein or polypeptide on the cell surface.

Preferably, the nucleic acid encoding the fusion protein is operably linked to control sequences to direct its expression. An example of this is a Lactococcus host organism further transformed with nucleic acid comprising a T7 or T7-like polymerase gene under the control of an inducible promoter effective in the Lactococcus host, wherein the control sequences comprise a promoter specific for said polymerase provided upstream of the nucleic acid encoding the fusion protein whereby the promoter directs transcription of the nucleic acid encoding the fusion protein selectively as a result of the expression of the polymerase (see GB-A-2278358).

The high level of heterologous protein expression which can be achieved using the T7 polymerase system has been found to provide high levels of expression of the Protein A-fusion polypeptide on the surface of the bacteria. For many of the applications envisaged for the invention, the economics of the associated processes will be materially favoured by achieving the highest possible surface density of fusion molecules on the bacteria. However, for some applications the use of constitutive, or less active, promoters may give useful results, especially where lower levels of expression are required.

Numerous variations on the disclosed vectors could be routinely prepared by those skilled in the art using known techniques and the disclosure provided herein. Further, the proteins or polypeptides encoded by the nucleic acid sequences above may be modified by varying their amino acid sequence without substantially altering their properties, eg by manipulation of the nucleic acid or amino acid sequences through insertion, addition, deletion or substitution of one or more base pairs or amino acids. Such derivatives of the polypeptides disclosed herein are included within the present invention.

As mentioned above, the Gram-positive host organisms transformed with the nucleic acid encoding fusion proteins have a wide variety of applications as vaccines, to display biologically active molecules on cell surfaces, as adsorbents and to display enzymes on cell surfaces, eg for use as catalysts.

Thus, in a further aspect, the present invention provides Gram-positive host organisms wherein the desired protein or polypeptide includes at least one epitope to which it is desired to raise an immunological response. Preferably, the protein or polypeptide is an immunogen from a pathogen, an antigen or an adhesin.

In this aspect, the present invention also provides a vaccine comprising the above host organisms in admixture with a suitable carrier. The present invention also includes the use of the above Gram-positive host organisms in the preparation of a vaccine wherein the desired protein or polypeptide is an epitope to which it is desired to raise an immunological response. Preferably, the vaccines are administered intranasally or parenterally, or via other mucosal routes such as orally or vaginally.

In a further aspect, the present invention provides Gram-positive host organisms wherein the desired protein or polypeptide is a biologically active molecule. By way of example, the biologically active molecule may be a drug, a hormone, an enzyme, DNA/RNA binding protein, or a substance capable of performing secondary modifications (glycosylation, disulphide isomerisation) on other coexpressed and secreted proteins. Alternatively, the desired protein or polypeptide can be a targeted group, for instance antibodies, or fragments thereof, or adhesins specific for receptors.

In this aspect, the present invention also includes a pharmaceutical composition comprising the Gram-positive host organisms, and their use in methods of medical treatment.

In a further aspect, the present invention provides Gram-positive host organisms wherein the desired protein or polypeptide is a specific binding partner of a ligand. In this aspect, the present invention also includes the use of Gram-positive host organisms in a method of purification or separation of a ligand wherein the desired protein or polypeptide is a specific binding partner of the ligand, whereby the display of the specific binding partner on the surface of the organism allows the binding partner to bind to the ligand.

The invention also provides a way of immobilising the Gram-positive host organisms on a solid phase, eg by expressing streptavidin fused to a cell wall anchoring domain so that the streptavidin represented on the cell surface can bind to biotin immobilised on a solid phase. Thus, the present invention provides a method of immobilising a Gram-positive host organism of the invention which comprises bringing a host organism of this aspect of the invention into contact with a solid surface which has the ligand immobilised thereon. The present invention also provides a method for detecting complexes with a specific ligand (e.g. biotin or an immunoglobulin) by coexpressing a reporter activity such as a luciferase or a fluorescent protein in cells which also express on their surface the protein binding to the ligand to be detected (e.g. streptavidin or protein A).

In a further aspect, the present invention provides a Gram-positive host organism wherein the desired protein or polypeptide is an enzyme. This aspect of the invention also includes a composition comprising the Gram-positive host organism wherein the desired protein or polypeptide is an enzyme which has been expressed and displayed on the cell surface of the host, and the use of the composition in a reaction catalysed by the enzyme, for example a surface enzyme which can break down unwanted food components such as fat and cholesterol from the surrounding milieu.

In a further aspect, the present invention provides a method of screening a library of substances, such as antibodies or antigens or fragments thereof, comprising transforming Gram-positive host organisms with nucleic acid encoding a fusion of the substances and a cell wall anchoring domain, expressing the fusion so that the substance is displayed on the cell surface. The particular substance being screened for can then be detected using a recognition agent, eg labelled antibodies.

DETAILED DESCRIPTION

Live or inactivated bacterial vaccines and tools for the production of anti-polypeptide antibodies The invention may be used for the surface expression of antigens, adhesins and biologically active molecules in Gram-positive bacteria such as L. lactis. These bacteria are among those which have been proposed as vaccine delivery vehicles for mucosal immunisation (Wells et al, 1993). Antigens which are exposed on the bacterial cell surface may be more easily recognised by the immune system (than antigens which are only released following bacterial death and degradation) owing to the greater accessibility of surface antigens to their receptors on such antigen-recognising and processing cells as macrophages, dendritic cells and B lymphocytes. The surface expression of antigens and epitopes may therefore enhance the immunogenicity of antigens expressed by Gram-positive bacterial vaccines. Whole cells expressing antigen on their surface will also be useful immunogens for raising polyclonal and monoclonal antibodies in animals (Charbit et al, 1987).

Bacterial delivery of biologically active molecules

The surface expression of adhesins specific for receptors present on cells and/or tissues in the gut and other mucosal tissues (for example, the respiratory, uro-genital and nasal tracts), in addition to the expression of antigens and/or biologically-active molecules would enable the recombinant bacteria to be targeted to specific cells and tissues, eg neoplasia. Such targeting would increase the efficiency with which these bacteria can be used to deliver antigens and/or biologically active molecules to mucosal surfaces. In cases where the bacteria being used do not normally adhere to, or proliferate on, a particular mucosal surface, such targeting would increase the contact time between the bacteria and the mucosal surface, thus facilitating delivery and/or uptake of a molecule or molecules synthesised by the bacteria.

The surface expression of numerous biologically active molecules would have a wide range of applications in the therapy of disease, by the delivery of any of a large number of hormones, cytokines or other immunomodulatory molecules, cell receptors and/or their ligands, enzymes, cell-specific toxins. Such molecules could be co-expressed with invasins or other proteins which enable bacteria to enter cells and/or to be released into the cytoplasm from the endosome; thus the targeting of bacteria to cells, and to compartments within cells, are rendered feasible by means of this invention.

Additionally, surface ligands with adequate binding affinity could be used to enable the bacteria to be coated with a wide variety of desired molecules; for example, surface expression of a DNA or RNA binding protein could be used to permit the organisms to be coated in DNA or RNA. Such a process could find applications in gene therapy or nucleic acid vaccination.

Surface display of specific antigens, antibodies and ligands

The recent development of phage display technology has enabled specific antigens, antibodies and other ligands to be isolated from complex libraries by panning for recombinant bacteriophage expressing the counter-ligands which then adhere to an immobilised support containing the antigen, antibody or receptor of interest (Chiswell and McCafferty, 1992). An alternative approach would be to use Gram-positive bacteria for the surface presentation of proteins and peptides. The advantages to the bacterial display technology would be (i) bacteria expressing the desired ligand could be detected directly using a fluorescent counter ligand as a probe; these bacteria could then be obtained free of non-expressor cells using a FACS machine capable of sorting single bacteria. This procedure would avoid the need to propagate the phage to recover the cloned DNA sequence of interest (ii) higher density of surface protein expression is possible in bacteria compared to the phage systems and (iii) problems with the inability of certain recombinant phage to infect *E. coli* (so that they can be propagated) will not be encountered.

The use of bacteria as whole cell adsorbents

The use of affinity chromatography for the purification of biological products can frequently convert multi-step into single-step or near single-step procedures. This results in turn in a reduction in the complexity of downstream engineering processes associated with the recovery of biological products, and also means that large savings can be achieved in capital investment; operating costs can be reduced, and the products themselves can be recovered more rapidly. In fact, one of the best examples of this approach is the use of wild type *Staphylococcus aureus* to bind and purify antibodies.

Protein A found on the surface of the bacteria has a high affinity for the Fc domain of certain immunoglobulins and heat killed and chemically stabilised *S. aureus* cells have been routinely used for the purification of antibodies.

However, the need for an abundant supply of an immobilised form of the ligand can render affinity chromatography uneconomic.

The expression of the functional fragments of ligands or counter-ligands such as single chain antibodies, protein receptors, adhesion molecules etc on the surface of bacteria would enable these molecules to be replicated inexpensively by bacterial growth; entrapped bacterial cells could then be used to provide an inexpensive form of adsorbent.

Innocuous Gram-positive bacteria such as *L. lactis* do not contain the endotoxins present in *E. coli* which initially contaminate all recombinant products made in this bacterium, and which must be removed during the course of purification procedures. Hence, the use of Gram-positive bacteria for the surface display of ligands will not result in the contamination of products with endotoxins.

Enzyme coated bacteria as biocatalysts

Many enzymes made by Gram-positive bacteria and other organisms are secreted by these organisms into their environment, where they may mediate a variety of biochemical transformations. These chemical conversions can be essential for survival and growth, or they may enable the organisms to compete more effectively with other organisms in their environment.

The enzymes needed for nutritional purposes include, for example, those which can degrade biological polymers such as carbohydrates, lipids, nucleic acids and proteins into their substituents, and provide nutrients for the growing organism.

Secreted enzymes also perform a range of different functions, such as the biosynthesis of slimes and mucins (glycoproteins or proteoglycans) which enable bacteria and other organisms to fasten themselves to favourable surfaces in their environment. They may also inactivate antimicrobial substances such as antibiotics or toxins emanating from other organisms; and they may degrade toxic or recalcitrant substances left in the environment by geological or industrial processes.

Many of these secreted enzymes have industrial utility, but ideally need to be present in a solid phase, in order that liquid reactants passed over this phase can be subjected to catalytic conversion by the immobilised enzyme.

It is another vital aspect of this invention that it will improve the feasibility of using enzymes in industrial processes by providing—in the form of bacteria able to manufacture the enzymes in immobilised form—the active components need for such biotransformation processes.

The use of immobilised cells for the production of secreted proteins

The invention provides a method for the production of secreted proteins by Gram-positive bacteria which are attached to an immobilised support. For example, cells which are displaying streptavidin on their surface and also secreting an enzyme or other protein of interest could be attached to a biotin coated solid phase. One advantage of this approach is that the recovery of the growth medium containing the secreted protein of interest does not require centrifugation to remove the bacterial cells.

Assembly at the bacterial surface of heterodimeric proteins with bifunctional aminoterminal domains In this aspect of the invention, one partner of the heterodimer, eg a fusion polypeptide comprising a signal peptide, a single chain antibody, the hinge and/or constant domains of the heavy chain and the cell wall anchoring domain of the Staphylococcus aureus protein A, is expressed at the bacterial surface and the other partner is secreted and composed of a similar fusion polypeptide, eg a different single chain antibody (recognizing a different antigen) or an enzymatic activity, but is devoid of the cell wall anchor. The constituent partner polypeptides may be synthesized either in the same engineered cell or in differently engineered cells grown in co-culture.

In this example, the bacterial surface acts as an assembly site for exclusively heterodimeric molecules having bifunctional aminoterminal domains. The assembled proteins may then be specifically released and purified from the collected bacteria, eg by the action of lysostaphin. Alternatively and preferentially, release may be obtained by the action on whole bacteria of a specific protease, eg factor Xa, enterokinase, collagenase, Igase (from Neisseria gonorrhoeae, thrombin, TEV (Tobacco Etch Virus) protease, the recognition site of which was incorporated into the fusion polypeptide just upstream of the cell wall anchor. The desired proteins may be purified by conventional separation techniques.

Although methods for producing bifunctional heterodimers are known, there are at present no generally applicable methods available for separating them from the unavoidably co-produced homodimeric (hence monofunctional) molecules.

Additionally, this method could be used for the assembly of homo-multimeric proteins on the surface of a bacteria.

EXAMPLE 1

Construction of Expression Plasmids

Stage 1: Cloning of S. aureus protein A anchoring domain

A DNA fragment encoding the Staphylococcus protein A (SPA) anchor of S. aureus strain Cowan I NCTC 8530 was obtained by the polymerase chain reaction (PCR) using primers based on the published sequence (Saiki et al. 1985). The PCR was performed with the thermostable Vent DNA polymerase (New England BioLabs) in a 100 $\mu$l of the buffer supplied by the manufacturer containing 2.5 mM each of dATP, dTTP, dCTP and dGTP, 1 $\mu$M of the sense (and antisense primers and 1 $\mu$g of genomic DNA isolated from S. aureus strain Cowan I NCTC 8530 by the method of Marmur et al., (1961). The sense and antisense primers were designed to include restriction endonuclease sites for BamHI and XbaI at their 5' ends respectively to facilitate the subsequent cloning steps. After 20 cycles of denaturation (94° C. for 45 seconds) primer annealing (68° C. for 30 seconds) and DNA polymerisation (72° C. for 45 seconds) a PCR amplified DNA product of the expected size (621 bp) was detected by agarose gel electrophoresis. The purified DNA fragment was then cloned and sequenced using standard procedures (Maniatis). The DNA sequence of the cloned DNA fragment encoding the C terminal region (nt 1043 to 2252) of S. aureus protein A was identical to that previously reported (Shuttleworth et al).

Stage 2: Cloning and manipulation of the streptavidin gene

Streptavidin was chosen as a reporter protein to demonstrate the feasibility of the present invention. Streptavidin is easily detected and is known to bind biotin for which antisera are commercially available. The streptavidin gene fragments were obtained from a series of plasmids in which the streptavidin gene had been mutated to incorporate different restriction endonuclease sites at the start and end of the coding sequence of the mature protein.

Figure 1:
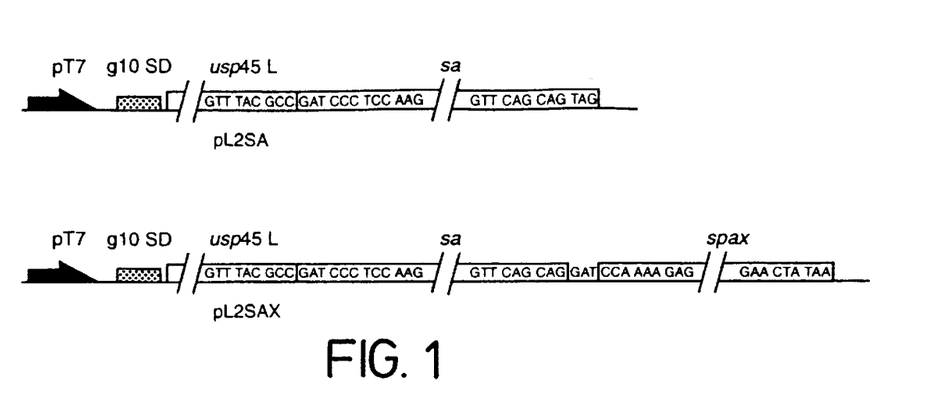
FIG. 1 shows the construction of the gene fusions described below.

A gene fragment encoding the mature form of streptavidin was ligated into NaeI digested L. lactis expression plasmid pLET2N (Steidler et al., 1995) to generate in frame fusion of the usp45 signal secretion signal leader (present in pLET2N) and the streptavidin coding sequence (FIG. 1). The resulting plasmid, designated pL2SA, can be used to express and secrete streptavidin in L. lactis (see below). Plasmid pL2SAX containing the S. aureus protein A C terminal anchoring domain (referred to as the X domain) fused to the 3' end of the streptavidin gene in pL2SA was then constructed by cloning the PCR amplified DNA fragment encoding the protein A anchor region (see stage 1 and FIG. 1). A lactococcal expression strain harbouring pL2SAX expresses a streptavidin—protein A C-terminal domain fusion protein which is firmly attached to the cell wall (see below).

Expression of streptavidin and streptavidin protein A fusion proteins in L. lactis Plasmids pL2SA and pL2SAX were isolated from E. coli strain MC1022 and used to transform the L. lactis T7 expression host strain MG1820 harbouring pILPol (strain UCP1000; Wells et al., 1993) by electroporation. Expression of the streptavidin and streptavidin—protein A fusion protein was induced in L. lactis by replacing lactose for glucose in the growth medium (Steidler et al., 1995). In order to detect expression of the streptavidin protein products in L. lactis, cellular fractionation and immunoblotting were performed with cells which had been induced for 3 hours. Ten ml of cells were first pelleted by centrifugation and the supernatant centrifuged a second time at 100 000 g for 1 hour to remove any insoluble material. Protein factions were then recovered from the high speed supernatant by phenolic extraction as previously described (Steidler et al., 1995). The cell pellets obtained in the first step were washed three times in Tris buffered saline (TBS: 0.15 M NaCl, 0.02 M Tris-HCl pH 7.5) and resuspended in 250 $\mu$l of 10% sucrose, 20 mM Tris-HCl (pH 7.5) containing 0.6 mg of lysostaphin (Sigma, St. Louis, USA) and incubated for 1 hour at 37° C. to enzymatically digest the cell wall.

After treatment with lysostaphin, the cells (referred to as the residue) were separated from the enzymatically released cell wall material by centrifugation and lysed by boiling in Laemmli cracking buffer. The supernatants referred to as the "lysostaphin released protein fractions" were similarly treated with cracking buffer. The proteins recovered from the growth medium, lysostaphin released fractions and cell residues were analysed by immunoblotting with antisera to streptavidin using standard procedures. Lysostaphin has been shown to specifically release proteins which are linked to the pentaglycine peptide present in the peptidoglycan of the cell wall (Schneewind et al, 1993).

The results of cell fractionation and immunoblotting of proteins recovered from L. lactis expression strain UCP1000 harbouring pL2SA showed that a protein of the expected size for streptavidin was produced and secreted into the growth medium by L. lactis. Streptavidin was not detected in the total cell protein residues of cells treated with lysostaphin and only trace amounts of protein were detected in the lysostaphin released cell wall material (see FIG. 2). In this strain, the relatively small proportion of the total amount of secreted streptavidin released by treatment of the cells with lysostaphin may be a consequence of streptavidin which has not diffused through the cell wall after transport across the cell membrane.

Figure 2:
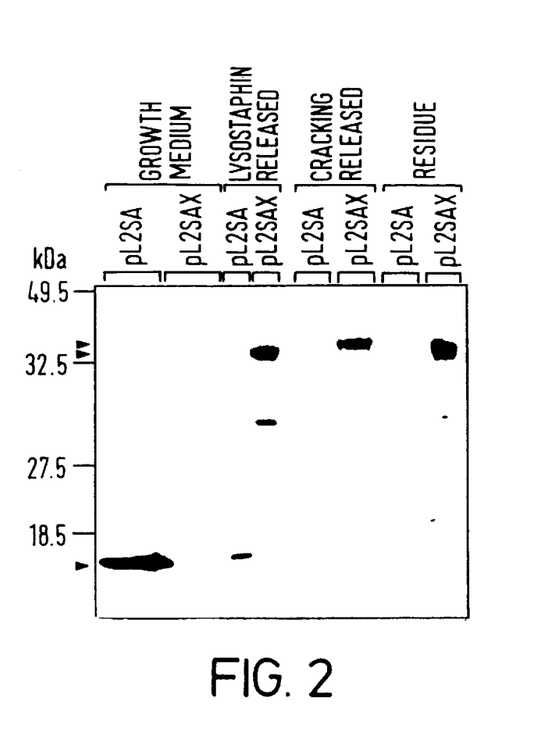
FIG. 2 shows a Western blot of proteins recovered from (i) the growth medium, (ii) the supernatant of lyostaphin treated cells, (iii) intact cells boiled in Laemmli SDS buffer "cracking released" and (iv) the residue of cell pellet of the lyostaphin treated cells. The proteins indicated (see arrow heads) were detected by immunoblotting with rabbit anti-streptavidin antiserum and a second antibody conjugate according to standard procedures. These results demostrate that the streptavidin protein fusion A protein produced in L. lactis is firmly attached to the cell surface.

In contrast to these findings, the streptavidin—protein A fusion protein produced by the strain carrying pL2SAX was not secreted into the growth medium. This fusion protein was however, present in substantial amounts in the material released from the cell wall by treatment with lysostaphin indicating that it had become associated with the cell wall (FIG. 2). The fusion protein was also detected in the pellet (residue) of lysostaphin treated cells suggesting that a proportion of the released protein had not diffused out of the cell wall during the incubation with lysostaphin. When washed cells expressing the streptavidin protein A fusion protein were boiled in Laemmli cracking buffer the protein detected by immunoblotting had an apparent molecular weight which was higher than the protein detected in the supernatant of the fraction of cells treated with lysostaphin (FIG. 2). This higher molecular weight polypeptide may represent an intermediate in the pathway which sorts and anchors the fusion protein to the cell wall. Both forms of the protein are found in the boiled cell pellet (residue) fraction of the lyostaphin treated cells, indicating that the more gentle enzymatic treatment of the cells with lyostaphin does not release the higher molecular weight form of the fusion protein into the supernatant.

Display of streptavidin on the surface of *L. lactis*

Figure 3:
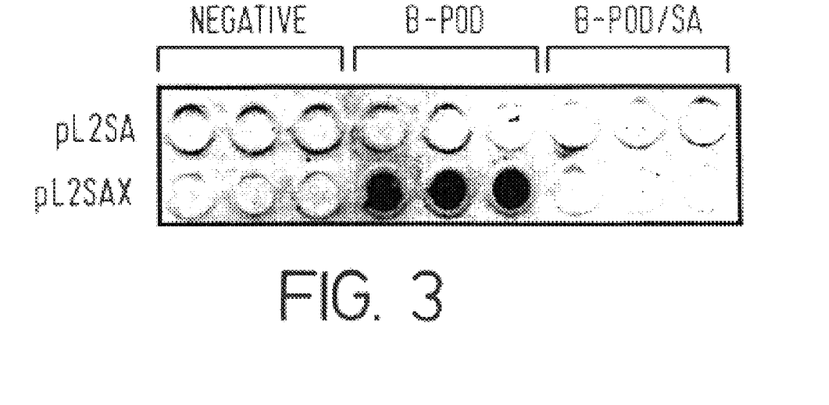
FIG. 3 shows that a biotin conjugate was able to specifically bind to the surface of intact cells expressing a streptavidin—protein A fusion, thus demonstrating that the protein is present on the surface of the cell. This figure shows a filter onto which cells expressing the strepavidin protein A fusion (pL2SAX) or streptavidin (pL2SA) have been collected and reacted with biotinylated horseradish peroxidase (B-POD) or B-POD which had been previously treated with streptavidin (SA) to block its binding sites (see wells labelled B-POD/SA). The cells binding B-POD were detected by incubation with a chromagenic substrate for horseradish peroxidase. Only the intact cells expressing the streptavidin protein A fusion protein on their surface bound the biotinylated enzyme conjugate B-POD.

In order to show that the fusion of streptavidin to the C terminal domain of *S. aureus* protein A would result in the display of the expressed protein on the cell surface, strains of *L. lactis* expressing streptavidin or the streptavidin protein A fusion product were washed three times in TBS containing 1% bovine serum albumin (BSA) and then incubated with biotinylated horseradish peroxidase (1 μg) for 1 hour at room temperature. Control samples of cells were also incubated with biotinylated horseradish peroxidase in the presence of soluble streptavidin to show that the binding to cells could be blocked by competition with the free substrate. The cells were then washed three times with TBS containing 1% BSA and harvested onto a cellulose nitrate filter by means of a vacuum apparatus. The binding of biotin to the cell surface was detected by incubating the filter in a solution of TMB (horseradish peroxidase substrate) according to the manufacturer's recommendations. The results in FIG. 3 show that the biotin horseradish peroxidase conjugate bound the surface of intact cells expressing the streptavidin protein A fusion protein but not to cells expressing streptavidin. The possibility that the biotin—horseradish peroxidase conjugate binds non-specifically to the cell surface of *L. lactis* expressing the streptavidin protein A fusion protein can be ruled out as binding was inhibited in the presence of soluble streptavidin.

Figure 4:
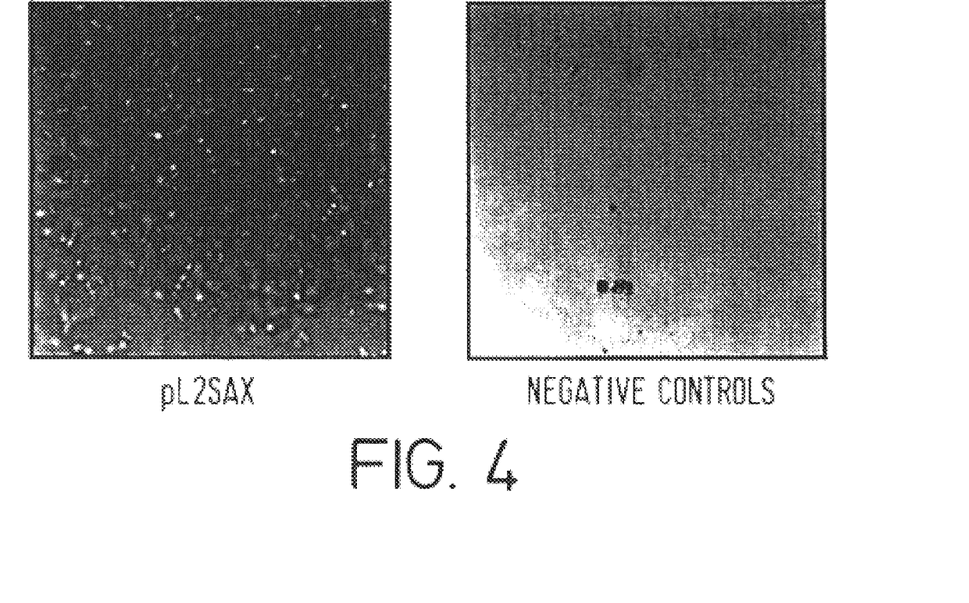
FIG. 4. The panel labelled pL2SAX shows a photograph of L. lactis cells expressing the streptavidin protein A fusion on their surface which have bound to a polystyrene surface coated with a biotinylated horseradish peroxidase conjugate. No cells are seen in the negative control which is representative of all the control samples described in the text.

Specific immobilisation of *L. lactis* cells expressing streptavidin on their cell surface To provide a solid surface for the specific binding of the bacterial cells expressing streptavidin on their cell surface Petri dishes (20 mm, Maxisorp, Nunc, Denmark) were coated with 1 μg/ml of biotinylated alkaline phosphatase (Boehringer Mannheim, Germany) for 1 hour in 1 ml of TBS at room temperature. Non-specific binding sites were then blocked by incubating the plates with 2 ml of TBS containing 1% BSA for 2 h at room temperature. 10 ml of cells expressing either streptavidin or the streptavidin protein A fusion protein were washed three times in TBS and resuspended in 1 ml of TBS containing 1% BSA for 1 hour at room temperature. During this incubation step the cells were kept in suspension by shaking for 6 seconds every minute. Finally, the cell suspension was diluted to 10 ml with TBS and 1 ml of this suspension added to the pre-treated petri dishes (see above) for 1 hour at room temperature. The petri dishes were then washed three times with 1 ml of TBS for ten min on an orbital shaker before they were examined by light microscopy. The results (FIG. 4 & Table 1) show that *L. lactis* expressing the streptavidin protein A fusion protein bind to the surface of the petri dish coated with biotin-alkaline phosphatase but not to petri dishes which were untreated with this conjugate. Cells expressing and secreting streptavidin did not bind to the surface of coated or uncoated petri dishes. The binding of cells expressing the streptavidin protein A fusion product was blocked by the addition of soluble streptavidin indicating that the binding was specific and mediated through the binding of biotin to the streptavidin present on the surface of the cells (Table 1).

TABLE 1 results of surface binding assays

| | Surface treatments | | |
|---|---|---|---|
| Strain of *L. lactis* | (i) 1% BSA | (i) 1 μg/ml B-AP; (ii) 1% BSA | (i) μg/ml B-AP; (ii) 30 μg/ml SA (iii) 1% BSA |
| MG1820 (pILPol,pL2SA) | ND | ND | ND |
| MG1820 (pILPol,pL2SAX) | ND | 2 × 10$^5$mm$^{-1}$ | ND |

Legend to Table 1. The expression strains of *L. lactis* either carried plasmid pL2SAX and produced the streptavidin protein A fusion product or plasmid pL2SA and produced streptavidin, ND; none detected, B-AP; biotin-alkaline phosphatase conjugate, BSA; bovine serum albumin, SA; streptavidin.

EXAMPLE 2

Display of Tetanus Toxin Fragment C (TTFC) Antigen on the Surface of *L. lactis*

This additional example provides evidence that protein antigens can be firmly attached to the surface of *L. lactis* by constructing chimeric genes encoding a fusion protein which contains nucleic acid encoding (1) an N-terminal secretion signal (2) the protein antigen to be surface expressed and (3) the cell wall sorting and anchoring domain of *S. aureus* protein A.

Stage 1: Cloning and genetic manipulation of TTFC and the *S. aureus* protein A anchoring domain.

(1a) Construction of pTREX and pTREX1

Synthetic oligonucleotides encoding a putative RNA stabilising sequence, a translation initiation region and a multiple cloning site for target genes were annealed by boiling 20 μg of each oligonucleotide in 200 ul of 1×TBE, 150 mM NaCl and allowing to cool to room temperature. Annealed oligonucleotides were extended using Tfl DNA polymerase in 1×Tfl buffer containing 250 μM deoxynucleotide triphosphates and 1.5 mM MgCl2 at 35° C., 45° C., 55° C. and 65° C. each for 1 minute followed by 10 minutes at 72° C. The sense and antisense oligonucleotides contained the recognition sites for NheI and BamHI at their 5' ends respectively to facilitate further cloning.

Figure 5A:
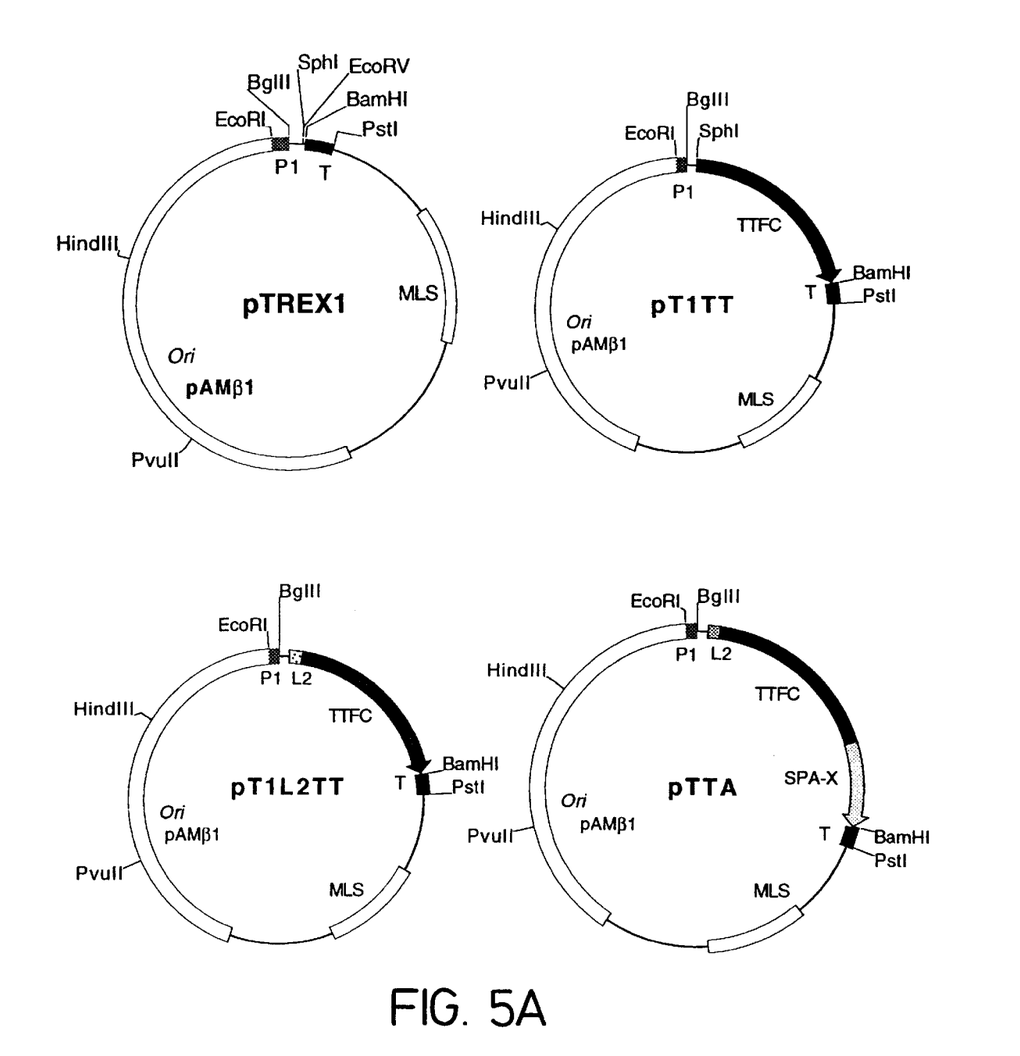
FIG. 5(A) shows physical and genetic maps of the broad Gram-positive host range vector pTREX1, pTIL2TT and PTITT. The expression cassette, macrolides, lincosamides and streptogramin B (MLS) resistance determinant, TTFC gene, secretion signal sequence of usp45 (L2), S. aureus protein A anchor (SPA-X) and the replicon (Ori- 'from pAMβ1') are depicted as thick lines.
Figure 5B:
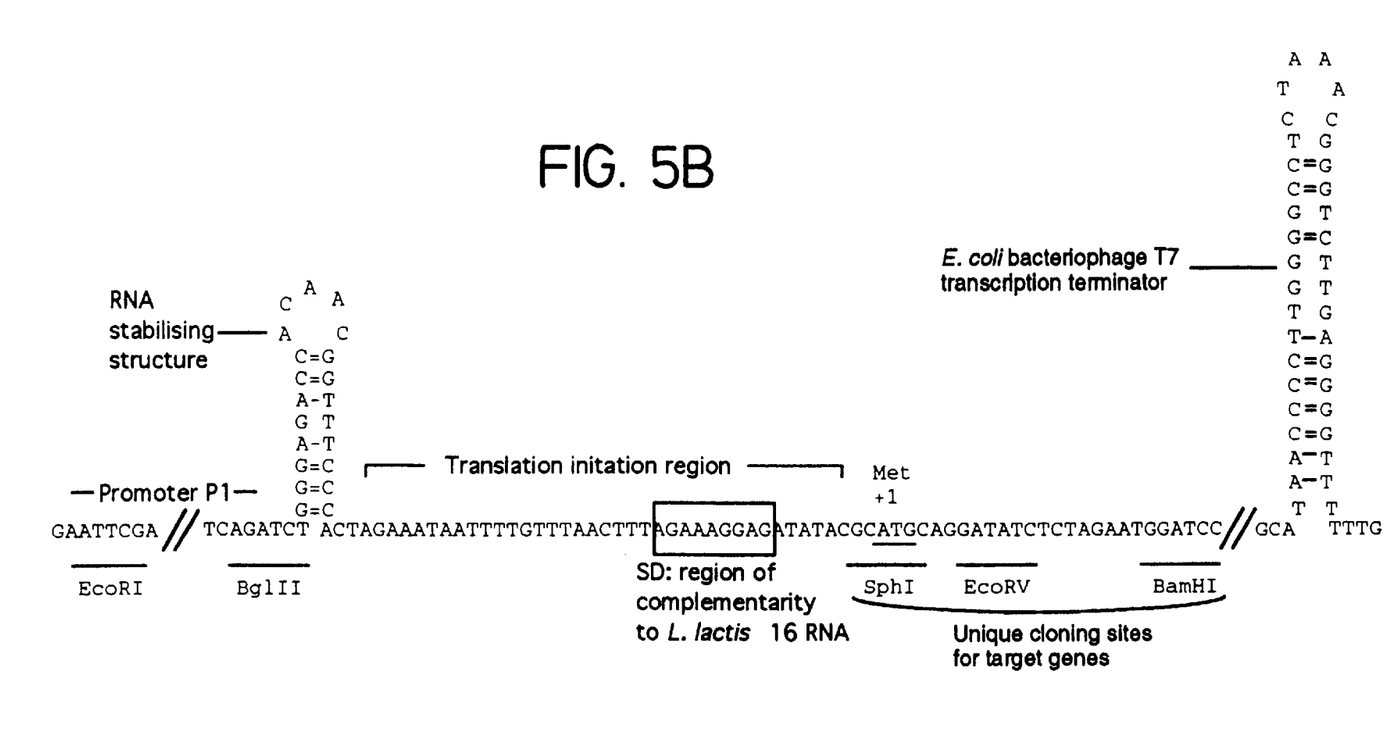
FIG. 5(B) is a schematic representation of the expression cassette in pTREX1 showing the various sequence elements involved in gene expression, the location of unique restriction endonuclease sites, Shine Dalgarno (SD) motif and translation initiation start codon (ATG)
Figure 5C:
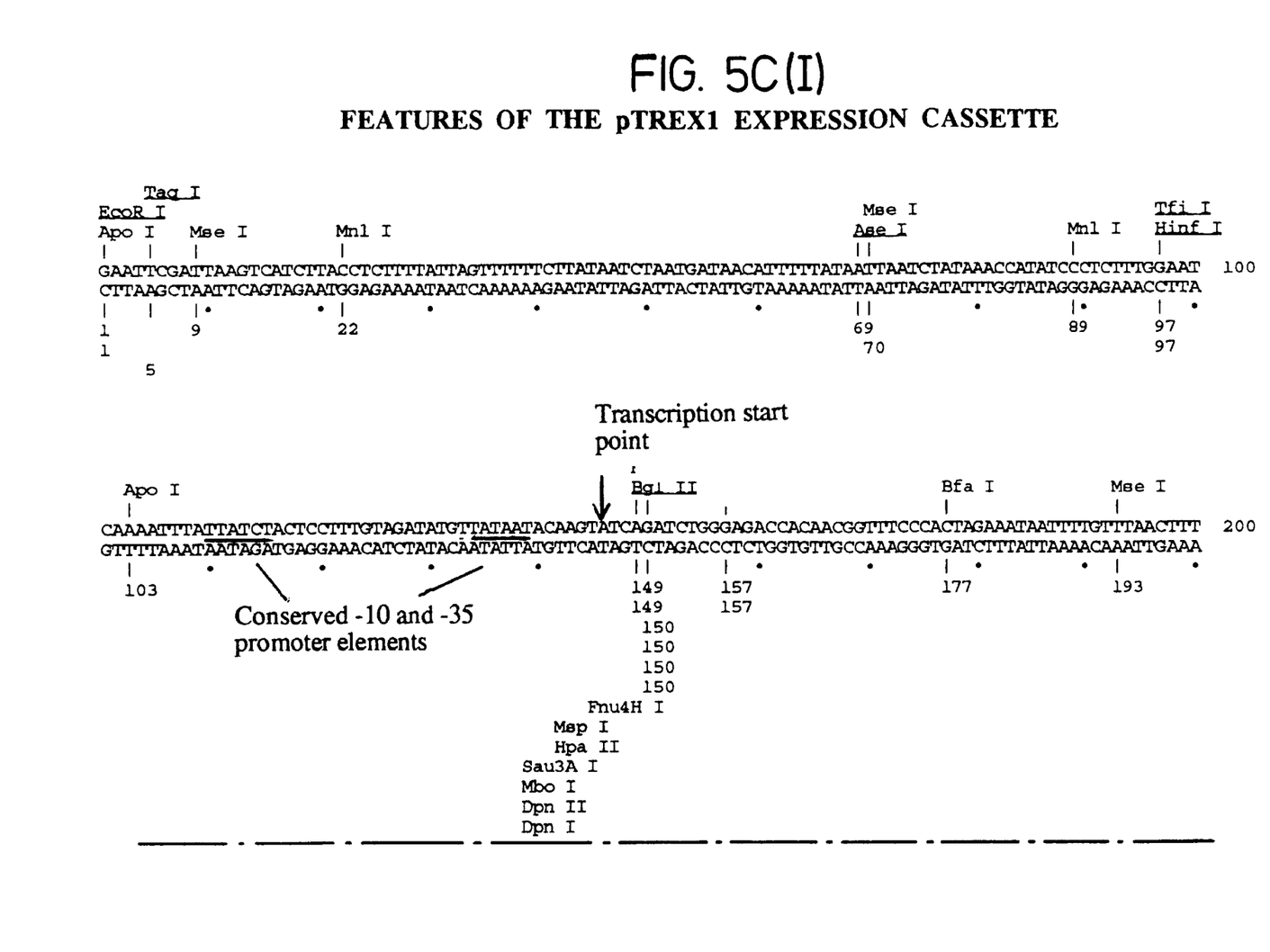
FIG. 5(C) shows the DNA sequence and restriction endonuclease site map of the pTREX1 expression cassette. The key expression elements are also indicated on the map.

The resulting ds DNA fragment was cut with NheI and BamHI, and cloned between the XbaI and BamHI sites in pUC19NT7, a derivative of pUC19 which contains the T7 expression cassette from pLET1 (Wells et al., 1993c) cloned between the EcoRI and HindIII sites. The resulting construct was designated pUCLEX. The complete expression cassette in pUCLEX was then removed by cutting with HindIII and blunting followed by cutting with EcoRI before cloning into the EcoRI and SacI (blunted) sites of pIL253 to generate the vector pTREX. In order to construct the expression vector pTREX1 a PCR amplified DNA fragments containing the lactococcal promoter P1 was cloned between the EcoRI and BglII sites present in the expression cassette of vector pTREX (FIG. 5). This promoter had been previously isolated using the promoter probe vector pSB292 and characterised by primer extension and DNA sequencing analysis (Waterfield et al., 1995).

(1b) Construction of plasmid pT1L2TT

A DNA fragment encoding the tetanus toxin fragment C gene fused to the lactococcal signal secretion leader sequence of the usp45 gene was obtained by the polymerase chain reaction (PCR) using plasmid pLET2-TTFC as a template and the published sequences (Wells et al., 1993b). The PCR was performed with the thermostable vent DNA polymerase (New England Biolabs) in a 100 μl of the reaction buffer supplied by the manufacturer containing 2.5 mM each of dATP, dTTP, dCTP, and dGTP, 1 μm of the sense and antisense primers (Figure X) and approximately 50 ng of plasmid pLET2-TTFC as template DNA. The antisense primer was designed to include a BamHI site at its 5' end to facilitate the subsequent cloning steps. After 30 cycles of denaturation (94° C. for 45 seconds), primer annealing (50° C. for 30 seconds) and DNA polymerisation (72° C. for 120 seconds) a PCR amplified DNA product of the expected size (1478 bp of double stranded DNA) was detected by agarose gel electrophoresis. The purified DNA fragment was then digested with restriction endonuclease BamHI and cloned into lactococcal expression plasmid pTREX1 which had first been cut with SphI blunted and then cut with BamHI. The resulting plasmid designated pT1L2TT is shown in FIG. 5.

(1c) Construction of pT1TT

A fragment of tetanus toxin fragment C (TTFC) was generated by PCR (using standard conditions; see above) which encoded XbaI and BamHI sites at the 5' and 3' ends respectively. A stop codon was introduced at the 3' end of the TTFC sequence before the BamHI site. The TTFC PCR fragment was first cloned between the XbaI and BamHI sites of pUCLEX and then removed by cutting with SphI-BamHI and recloned intoSphI and BamHI digested pTREX1. The resulting plasmid designated pT1TT is shown in FIG. 5.

(1d) Construction of pTTA

Figure 6:
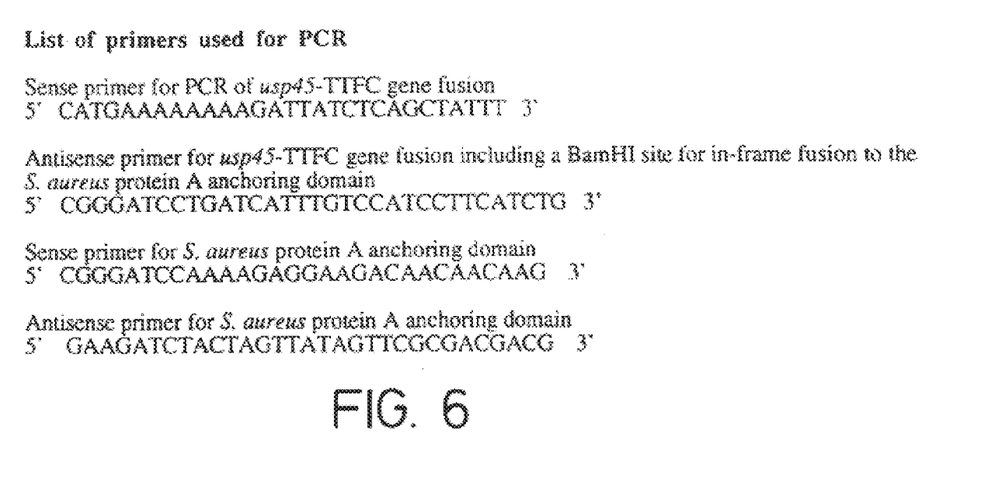
FIG. 6 shows the list of primers used for PCR.

A DNA fragment encoding the Staphylococcus protein A (SPA) anchor of S.aureus strain Cowan I NCTC 8530 was obtained by PCR using primers based on the published sequence (Figure X). The sense and antisense primers were designed to include restriction endonuclease sites for BamHI and BglII at their 5' ends respectively to facilitate the subsequent cloning steps. The PCR was performed with the thermostable vent DNA polymerase (New England Biolabs) in a 100 μl of the reaction buffer supplied by the manufacturer containing 2.5 mM each of dATP, dTTP, dCTP, and dGTP, 1 μm of the sense and antisense primers (FIG. 6) and approximately 50 ng of plasmid pL2SAX (further described in this patent) as template DNA. After 30 cycles of denaturation (94° C. for 45 seconds), primer annealing (55° C. for 30 seconds) and DNA polymerisation (72° C. for 35 seconds) a PCR amplified DNA product of the expected size was detected by agarose gel electrophoresis. The purified DNA fragment was then digested with restriction endonucleases BamHI and BglII and cloned into plasmid pT1L2TT which had first been cut with BamHI and dephosphorylated using calf intestinal phosphatase (Boehringer Mannheim) according to the methods recommended by the manufacturer. The resulting plasmid designated pTTA contains the S.aureus protein A C terminal domain (referred to as the X domain) fused to the 3' end of the TTFC gene (FIG. 5).

Stage 2: Expression and surface display of the TTFC-protein A fusion protein in L. lactis.

Figure 7:
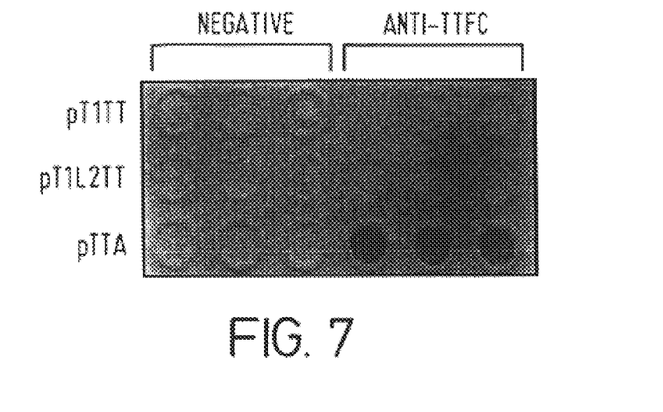
FIG. 7 shows a filter onto which intact cells expressing TTFC intracellularly (pTITT), secreting TTFC (pTIL2TT) or expressing a TTFC-protein A fusion protein (pTTA) have been incubated with rabbit TTFC polyclonal antisera, collected onto a membrane and then reacted with an antibody peroxidase conjugate and substrate to detect the binding of anti-TTFC antibody on the surface of the cells. Only the intact cells expressing the TTFC-protein A fusion displayed TTFC on their cell surface.

In order to show that the fusion of TTFC to the C terminal domain of S.aureus protein A would result in the display of the expressed protein on the cell surface, strains of L. lactis expressing TTFC intracellularly (i.e. carrying plasmid pT1TT), secreting TTFC (i.e. carrying plasmid pT1L2TT) or theTTFC protein A fusion product (i.e. carrying plasmid pTTA) were harvested by centifugation, washed three times in TBS (20 mM Tris-HCl pH 7.5, 150 mM NaCl) containing 1% BSA and then incubated with 1 μg of rabbit-anti-TTFC for 30 min at room temperature. The cells were then washed three times with 1 ml of TBS and resuspended in 1 ml of TBS. The cells in 100 μl of this cell suspension were harvested onto a cellulose nitrate membrane (0.22 μm) by means of a vacuum apparatus. The membrane was then incubated for 1 hour at room temperature in 5 ml of PBS-2.5% skim milk powder containing 5 μg of anti rabbit IgG conjugated to horse raddish peroxidase (Boehringer Manheim). The binding of the anti rabbit peroxidase to rabbit anti TTFC antibodies bound on the surface of intact cells of L.lactis carrying pTTA but not pT1L2TT and pT1TT was detected by incubating the filter in a solution of of TMB (horseradish peroxidase substrate) according to the manufacturer's recommendations. The results shown in FIG. 7 indicate that TTFC is only detected on the surface of intact cells expressing the TTFC protein A fusion protein.

REFERENCES

Charbit et al, J. Bacter., 173(1): 262–275, 1991
Charbit et al, J. Immunol. 139: 1658–1664, 1987
Chiswell and McCafferty, Trends Biotechnol. 10: 80–84, 1992
Georgio, G et al, TIBTECH 11: 6–10, 1993
Klauser et al, EMBO J. 9: 1991–1999, 1990
Kornacker and Pugsley Mol. Micro. 7: 1101–1109, 1990b
Kornacker and Pugsley Annu Rev. Genet. 24: 59–72, 1990a
Mamur, J. Mol. Biol., 3:208–218, 1961
Maniatis et al, Molecular Cloning: A Laboratory Manual. Cold Spring Harbor, N.Y.: Cold Spring Harbor Laboratory Press
Navarre and Schneewind Mol. Micro. 14(1): 115–121, 1994
Pohlner et al, Nature 352: 458–462, 1987
Saki et al, Science 230: 1350–1354, 1985
Schneewind et al, EMBO J 12(12): 4803–4811, 1993
Shuttleworth et al, Gene 56:283–295, 1987
Simon, D. and Chopin, A., *Biochimie* 70: 559–567 (1988)
Steidler et al, Mol. Gen. Genet. 236: 187–192, 1993a
Steidler et al, J. Bact. 175(23): 7639–7643, 1993b
Steidler et al, Appl. Environ. Microbiol. 61: 1627–1629, 1995
Thiry et al, Appl. Environ. Microbiol. 55:984–993, 1989
Waterfield, N. R., Le Page, R. W. F., Wilson, P. W. and Wells, J. M., *Gene.* 165: 9–15 (1995).
Wells et al, Mol. Microbiol. 8: 1155–1162, 1993
Wells, J. M., Wilson, P. W., Norton, P. M., Gasson, M. J. and Le Page, R. W. F., *Molec. Microbiol.* 8: 1155–1162 (1993a)
Wells, J. M., Wilson, P. W., Norton, P. M. and Le Page, R. W. F., *Environ. Microbiol.* 59: 3954–3959 (1993b)
Wells, J. M., Wilson, P. W. and Le Page, R. W. F., *J. Appl. Bact.* 74: 629–636 (l993c)

What is claimed is:

1. A recombinant vector including nucleic acid encoding a fusion protein comprising a secretion signal sequence obtained from the signal sequence of the protein usp45, a desired protein or polypeptide and a cell wall attachment domain comprising of at least the C-terminal anchoring domain obtained from *staphylococcus aureus* protein A so that when a *lactococcus lactis* host organism is transformed with the vector and the fusion protein is expressed, the desired protein or polypeptide is attached and displayed on the outer surface of the cell wall of the host.

2. A recombinant vector as claimed in claim 1 wherein the nucleic acid encoding the fusion protein is operably linked to control sequences which direct its expression.

3. A recombinant vector as claimed in claim 2 wherein the nucleic acid further comprises a T7 polymerase gene under the control of an inducible promoter provided upstream of the nucleic acid encoding the fusion protein.

4. A *lactococcus lactis* host organism transformed with a recombinant vector encoding a fusion protein comprising a secretion signal sequence, a desired protein or polypeptide and a cell wall attachment domain comprising at least the C-terminal anchoring domain obtained from *staphylococcus aureus* protein A so that when the fusion protein is expressed, the desired protein or polypeptide is attached and displayed on the outer surface of the cell wall of the host.

5. A *lactococcus lactis* host organism is defined in claim 4 wherein the desired protein or polypeptide has been expressed, and as covalently attached to the cell wall and is displayed on the outer face of the surface of the host organism.

6. A method of engineering a *lactococcus lactis* host organism to display a desired protein or polypeptide on its surface comprising transforming *lactococcus lactis* with recombinant nucleic acid encoding a fusion protein comprising a secretion signal sequence, a desired protein or polypeptide and a cell wall attachment domain comprising at least the C-terminal anchoring domain obtained from *Staphylococcus aureus* protein A, so that *lactococcus lactis* is capable of expressing the fusion protein, whereby the cell wall attachment domain enables the lactococcus lactis to attach and display the desired protein or polypeptide on the cell wall surface.

7. A *lactococcus lactis* host organism, as defined in claim 4 wherein the desired protein or polypeptide includes at least one epitope to which it is desired to raise an immunological response.

8. A *lactococcus lactis* host organism, as claimed in claim 7 wherein the desired protein or polypeptide is an immunogen from a pathogen, an antigen or an adhesin.

9. A vaccine comprising a *lactococcus lactis* host organism as defined in claim 7 in admixture with a suitable carrier.

10. A *lactococcus lactis* host organism as defined in claim 4 wherein the desired protein or polypeptide is one for which it is desired to elicit tolerance.

11. A *lactococcus lactis* host organism as defined in claim 4 or claim 5 wherein the desired protein or polypeptide is a biologically active molecule that is a drug, a hormone, an enzyme, DNA/RNA binding protein or a substance capable of performing secondary modifications on other coexpressed and secreted proteins.

12. A *lactococcus lactis* host organism as defined in claim 4 wherein the desired protein or polypeptide is a targeting group capable of directing binding of the host organism to a target site.

13. A *lactococcus lactis* host organism as claimed in claim 11 wherein the targeting group is (a) an antibody, or fragment thereof, which is capable of binding to a target antigen, (b) an antibody, or fragment thereof, which is capable of binding to a hapten or (c) is an adhesin.

14. A pharmaceutical composition comprising a *lactococcus lactis* host organism as defined in claim 4 in admixture with a suitable carrier.

15. A *lactococcus lactis* host organism as defined in claim 4, wherein the desired protein or polypeptide is a specific binding partner of a ligand.

16. A *lactococcus lactis* host organism as claimed in claim 15 wherein the ligand is bound to a solid surface such that the host organism will be immobilised thereon.

17. A *lactococcus lactis* host organism as claimed in claim 16 wherein the desired protein or polypeptide is streptavidin and the ligand is Biotin or a Biotin conjugate.

18. A *lactococcus lactis* host organism as defined in claim 4 wherein the desired protein or polypeptide is an enzyme.

19. A composition comprising a *lactococcus lactis* host organism as defined in claim 18 wherein the enzyme has been expressed and is displayed on the cell surface of the host organism.

20. A *lactococcus lactis* host organism transformed with a recombinant vector as defined in claim 1.

21. A *lactococcus lactis* host organism as defined in claim 20 wherein the desired protein or polypeptide has been expressed, and is covalently attached to the cell wall and is displayed on the outer surface of the cell wall of the host organism.

22. A method as claimed in claim 6 wherein the secretion signal peptide is obtained from the signal sequence of the protein usp45.

23. A method as claimed in claim 6 wherein the nucleic acid encoding the fusion protein is operably linked to control sequences which direct its expression.

24. A method as claimed in claim 6 wherein the nucleic acid further comprises a T7 polymerase gene under the control of an inducible promotor provided upstream of the nucleic acid encoding acid encoding the fusion protein.

* * * * *

UNITED STATES PATENT AND TRADEMARK OFFICE
CERTIFICATE OF CORRECTION

PATENT NO.    : 6,190,662 B1
DATED         : February 20, 2001
INVENTOR(S)   : Lothar STEIDLER and Erik REMAUT Page 1 of 1

It is certified that error appears in the above-identified patent and that said Letters Patent is hereby corrected as shown below:

On line 3 of claim 5, please change "as covalently attached" to --is covalently attached--.

On line 10 of claim 6, please change "lcatococcus lactis to --*lactococcus lactis*--.

On lines 1-2 of claim 11, please change "as defined in claim 4 or claim 5" to --as defined in claim 4--.

On line 3 of claim 16, please change "immobilised" to --immobilized--.

On line 4 of claim 24, please change "nucleic acid encoding acid encoding" to --nucleic acid encoding--.

Signed and Sealed this

Fifth Day of June, 2001

*Attest:*

*Attesting Officer*

NICHOLAS P. GODICI
*Acting Director of the United States Patent and Trademark Office*